(12) United States Patent
Tretbar et al.

(10) Patent No.: US 10,765,403 B2
(45) Date of Patent: Sep. 8, 2020

(54) ULTRASONIC MEASURING DEVICE, EXAMINATION APPARATUS AND METHOD FOR OPERATING SAME

(71) Applicant: Fraunhofer-Gesellschaft zur Foerderung der angewandten Forschung, e.V., Munich (DE)

(72) Inventors: Steffen Tretbar, Saarbruecken (DE); Christian Degel, Blieskastel (DE); Matthias Guenther, Bremen (DE)

(73) Assignee: Franhofer-Gesellschaft zur Foerderung der angewandten Forschung, e.V., Munich (DE)

( * ) Notice: Subject to any disclaimer, the term of this patent is extended or adjusted under 35 U.S.C. 154(b) by 992 days.

(21) Appl. No.: 14/387,479

(22) PCT Filed: Feb. 18, 2013

(86) PCT No.: PCT/EP2013/000470
§ 371 (c)(1),
(2) Date: Sep. 23, 2014

(87) PCT Pub. No.: WO2013/139422
PCT Pub. Date: Sep. 26, 2013

(65) Prior Publication Data
US 2015/0065856 A1   Mar. 5, 2015

(30) Foreign Application Priority Data
Mar. 23, 2012   (DE) .................. 10 2012 005 895

(51) Int. Cl.
*A61B 8/00* (2006.01)
*G01R 33/48* (2006.01)
(Continued)

(52) U.S. Cl.
CPC .......... *A61B 8/4416* (2013.01); *A61B 5/0035* (2013.01); *A61B 5/055* (2013.01);
(Continued)

(58) Field of Classification Search
CPC . G01R 33/4814; A61B 8/4416; A61B 5/0035; A61B 5/055; A61B 8/145;
(Continued)

(56) References Cited

U.S. PATENT DOCUMENTS 5,394,877 A * 3/1995 Orr ...................... A61B 5/0408
600/459
5,458,140 A * 10/1995 Eppstein ............ A61B 5/14514
600/573
(Continued)

FOREIGN PATENT DOCUMENTS

DE   102010025857 A1 * 1/2012 ............ A61B 5/033
JP   2006230912        2/2005
(Continued)

OTHER PUBLICATIONS

"The safe use of equipment in the magnetic resonance environment." Health Devices, Dec. 2001; 30(12):421-44. (Year: 2001).*
(Continued)

*Primary Examiner* — Angela M Hoffa
*Assistant Examiner* — Helene Bor
(74) *Attorney, Agent, or Firm* — Caesar Rivise, PC

(57) ABSTRACT

The invention relates to an ultrasonic measuring device including an ultrasonic array configured to detect ultrasonic signals, and a housing. The housing includes an acoustic window portion and a housing wall. The ultrasonic array is arranged in the housing in acoustic contact with the acoustic window portion. The acoustic window portion is configured to adhere to a surface of the object to be examined. The invention further relates to an examination apparatus, which
(Continued)

Figure 1:
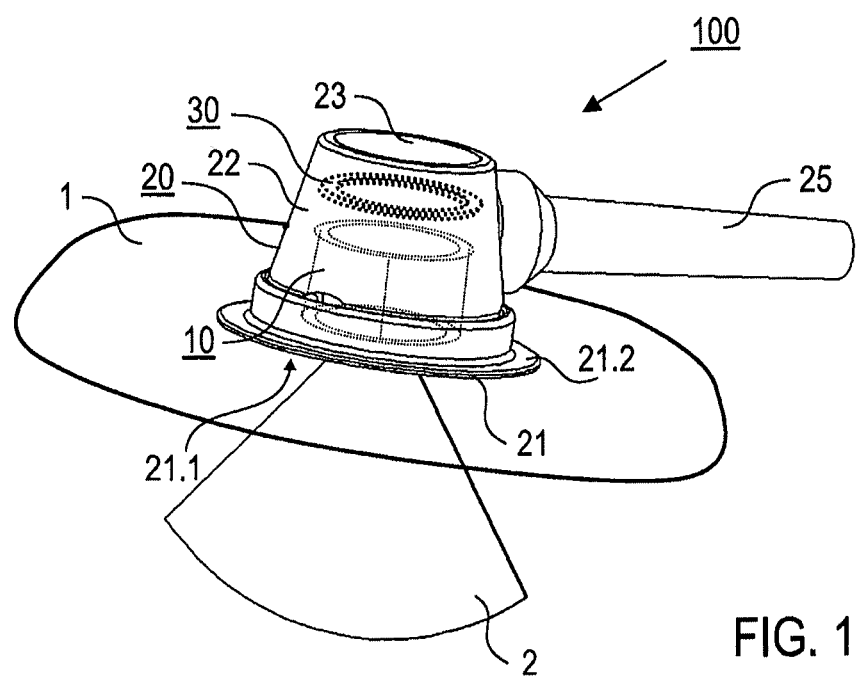

includes at least one such ultrasonic measuring device, and to a method for ultrasonic signal detection, in particular for ultrasound-based imaging.

16 Claims, 7 Drawing Sheets

(51) Int. Cl.
    *A61B 5/055*     (2006.01)
    *A61B 5/00*     (2006.01)
    *A61B 8/14*     (2006.01)
    *G01S 15/89*     (2006.01)
    *G01S 7/52*     (2006.01)

(52) U.S. Cl.
    CPC ............ *A61B 8/145* (2013.01); *A61B 8/4209* (2013.01); *A61B 8/4236* (2013.01); *A61B 8/4254* (2013.01); *A61B 8/4281* (2013.01); *A61B 8/4411* (2013.01); *A61B 8/4461* (2013.01); *A61B 8/4477* (2013.01); *A61B 8/4483* (2013.01); *A61B 8/4494* (2013.01); *G01R 33/4814* (2013.01); *A61B 5/0095* (2013.01); *A61B 8/4263* (2013.01); *G01S 7/52079* (2013.01); *G01S 15/894* (2013.01); *G01S 15/8915* (2013.01)

(58) Field of Classification Search
CPC ... A61B 8/4209; A61B 8/4236; A61B 8/4254; A61B 8/4281; A61B 8/4411; A61B 8/4461; A61B 8/4477; A61B 8/4483; A61B 8/4494; A61B 5/0095; A61B 8/4263; G01S 7/52079; G01S 15/8915; G01S 15/894
See application file for complete search history.

(56) References Cited

U.S. PATENT DOCUMENTS

| | | | |
|---|---|---|---|
| 5,598,845 A | 2/1997 | Chandraratna et al. | |
| 5,844,140 A * | 12/1998 | Seale | A61B 8/08 73/633 |
| 6,048,323 A * | 4/2000 | Hon | A61B 5/4356 600/588 |
| 7,945,304 B2 | 5/2011 | Feinberg | |
| 8,235,909 B2 * | 8/2012 | Barthe | A61B 8/14 600/463 |
| 2004/0064051 A1 * | 4/2004 | Talish | A61N 7/00 600/459 |
| 2005/0113684 A1 * | 5/2005 | Lokhandwalla | G01H 3/00 600/427 |
| 2007/0167705 A1 * | 7/2007 | Chiang | A61B 5/6805 600/407 |
| 2008/0252957 A1 * | 10/2008 | Thibout | H02N 2/108 359/223.1 |
| 2008/0262812 A1 * | 10/2008 | Arata | A61F 2/3859 703/11 |
| 2009/0321457 A1 * | 12/2009 | Baril | A61B 8/4209 220/600 |
| 2010/0152590 A1 | 6/2010 | Moore et al. | |
| 2010/0168577 A1 * | 7/2010 | Vezina | A61B 5/02028 600/443 |
| 2013/0158385 A1 * | 6/2013 | Barnes | G01R 33/4814 600/411 |
| 2013/0178732 A1 * | 7/2013 | Wedegaertner | A61B 5/033 600/413 |

FOREIGN PATENT DOCUMENTS

| | | |
|---|---|---|
| WO | 2004/064642 | 8/2004 |
| WO | 2008/042559 | 4/2008 |

OTHER PUBLICATIONS

Shokrollahi, P., 2017. Measuring the Temperature Increase of an Ultrasonic Motor in a 3-Tesla Magnetic Resonance Imaging System. Actuators, [online] 6(2). Available at: <https://www.mdpi.com/2076-0825/6/2/20/htm#B18-actuators-06-00020> [Accessed Jun. 20, 2020]. (Year: 2017).*

* cited by examiner

ULTRASONIC MEASURING DEVICE, EXAMINATION APPARATUS AND METHOD FOR OPERATING SAME

CROSS-REFERENCE TO RELATED APPLICATIONS

This national stage application claims the benefit under 35 U.S.C. § 371 of International Application No. PCT/EP2013/000470 filed on Feb. 18, 2013, entitled ULTRASONIC MEASURING DEVICE, EXAMINATION APPARATUS AND METHOD FOR OPERATING THE SAME, whose entire disclosure is incorporated by reference herein.

The invention refers to an ultrasonic measuring device with an ultrasonic array to detect ultrasonic signals which is arranged in a housing, in particular for imaging methods or methods for ultrasound-based measurement of sample properties. The ultrasonic measuring device is characterised in particular by an ultrasonic array which can be adjusted in the housing using an actuator. The invention furthermore refers to an examination apparatus which contains one or several ultrasonic measuring devices of this type. The invention furthermore refers to methods for ultrasonic signal detection using the ultrasonic measuring device, such as imaging methods or methods for ultrasound-based measurement of sample properties. The invention can in particular be used in medical imaging, in ultrasound-based sample treatment and for the destruction-free examination of samples.

The use of manually positioned ultrasonic measuring heads in medical imaging is generally known. An ultrasonic measuring head is manually placed on the desired body section by the user (doctor) and moved about on this area to find an ideal position for imaging. If the imaging is to be repeated for observation purposes, the ultrasonic measuring head must be fixed on the body section. The fixing of an ultrasonic measuring head using a mechanical holding arm is known from practice. However, this fixing is static and is usually unsuitable to provide reliable and comparable ultrasonic images if the object to be examined moves (e.g. through breathing, pulsating heart etc.). The area to be investigated may move away from the static imaging area of the ultrasonic measuring head defined by the fixing so that an analysis of the ultrasonic images obtained is impaired.

An ultrasonic measuring head is known from U.S. Pat. No. 5,598,845 A which can be positioned using adhesive tape on an area of a body section to be examined. The conventional ultrasonic measuring head comprises an ultrasonic array which is arranged in a housing. Ultrasonic waves from the ultrasonic array can be coupled into the area to be examined through an acoustic window portion of the housing and detected after back reflection using the ultrasonic array. The housing is positioned in a collar which, together with the adhesive tape which is arranged next to the acoustic window portion, can be fixed to the area to be examined. The alignment of the housing together with the ultrasonic array relative to the collar is adjustable in order to direct the sound field of the ultrasonic array to a specific area to be examined.

The conventional ultrasonic measuring head in accordance with U.S. Pat. No. 5,598,845 A has the following disadvantages. Firstly, the adhesive tape leads to problems in the positioning of the ultrasonic measuring head. For example, the adhesive tape may crease and stick to itself or to parts of the ultrasonic measuring head. Furthermore, there must be sufficient space also for the adhesive tape on the surface of the body section to be examined in addition to the acoustic window portion. A further disadvantage is that the ultrasonic array can be adjusted only together with the housing. This means that adjustment leads to a movement of the housing relative to the body section and therefore to an impairment of the fixing. Furthermore, the composition of housing and collar is a complex structure which is expensive and complicated to manufacture. If the ultrasonic measuring head is to be used on different patients, this will require a high level of cleaning which is increased by the complex structure. A further problem is the adjustment of the housing relative to the collar. For adjustment purposes pins which protrude outwards from the surface of the housing through the collar must be moved. Adjustment requires a manual intervention on the part of the user.

The conventional ultrasonic measuring head can therefore be used for applications to only a limited extent in which the area to be examined is to be recorded permanently and reliably over a lengthy time period such as for ultrasonic imaging, movement correction by way of ultrasound, for the effective control of radiotherapy systems, for ultrasonic therapy systems or other position-controlled interventions.

Another general problem of the conventional ultrasonic technology is to be found in multimodal imaging and in the control of therapy systems if the operation of the ultrasonic measuring head disturbs the complementary modality or the therapeutic method or conversely is disturbed by the modality or the therapeutic method. For example, there is an interest in combining the ultrasonic imaging with the MRT (Magnetic Resonance Tomography) imaging, whereby conventional ultrasonic measuring heads disturb the operation of the MRI apparatuses and are disturbed by the high-frequency fields in the MRI apparatus. No ultrasonic measuring head is currently known which is suitable for use in MRI apparatuses or during radiotherapy.

The problems specified refer not only to ultrasonic measurements in which ultrasonic signals are generated by coupling ultrasound into the area to be examined. The problems also arise, for example, in ultrasonic measurements in which the ultrasonic signals are excited by the coupling in of pulsed light (photoacoustic imaging).

The objective of the invention is to provide an improved ultrasonic measuring device using which the disadvantages of conventional techniques can be overcome and which in particular is suitable for a permanent and reliable fixing on an object to be examined, a reliable adjustment in the fixed state, a reduced sensitivity to outer disturbances and/or a reduced disturbing influence in the vicinity of the measuring device. A further objective of the invention is to provide an improved examination apparatus which is provided with at least one ultrasonic measuring device of this nature. It is furthermore an objective of the invention to provide an improved method of ultrasonic measurement in which the disadvantages of conventional techniques are avoided and which, in particular, is suitable for permanent and reliable, position-precise and/or interference-minimised measurement.

These objectives are solved by an ultrasonic measuring device, examination apparatus and methods with the features of the independent claims. Advantageous embodiments and applications of the invention result from the dependent claims.

In accordance with the first aspect of the invention, the above mentioned objective is solved by an ultrasonic measuring device which comprises a housing in which an ultrasonic array is arranged. The ultrasonic array comprises at least two ultrasonic transducer elements using which ultrasonic signals may be detected. The ultrasonic array has a predefined sensitivity characteristic which forms a spatial region adjacent to the ultrasonic array in which the ultrasonic signals can be detected in a directional manner or into which ultrasonic waves are radiated during operation of the ultrasonic array as emitter in a directed fashion. The sensitivity characteristic depends in particular on the position and/or orientation of the ultrasonic array relative to the object to be examined.

The housing comprises generally a component with a one-part or multi-part inner space in which the inventive ultrasonic array is arranged. The housing comprises a housing wall and an acoustic window portion. The acoustic window portion typically has the shape of a plane or curved, layer-shaped wall which is adapted for a transmission of ultrasonic waves. The acoustic window portion is a part of the housing through which the ultrasound from the ultrasonic array is directionally emitted into and/or received from the surrounding. The ultrasonic array is arranged in the housing in acoustic contact with the acoustic window portion.

According to the invention, the acoustic window portion is configured to adhere to a surface of the object to be examined. The external surface of the acoustic window portion is provided with an adhesive material. The acoustic window portion has at least one adhesive surface on the outer side of the housing. The acoustic window portion has an adhesion such that the housing with the components of the ultrasonic measuring device arranged therein can be reliably fixed to the surface of the object to be examined. The inventors have found that ultrasonic waves with the adhesive material can be coupled into and from the object to be examined through the acoustic window portion. A self-adhesive acoustic window portion is preferred. The adhesive material serves both to fix the ultrasonic measuring device and to conduct the sound. An additional acoustic transmission medium on the outer side of the housing is not necessary. The fixing of the ultrasonic measuring device on the object and the transmission of the ultrasonic signals through the acoustic window portion are preferably realised simultaneously. The disadvantages of adhesive strips are avoided. The ultrasonic measuring device has a compact design.

In accordance with a preferred embodiment of the invention, the acoustic window portion can be arranged detachably with the remaining housing. The acoustic window portion is connected detachably with the housing wall. For the purposes of sound transmission, gel, oil or fat can be provided between the separable parts. This advantageously facilitates a simple replacement of the acoustic window portion, e.g. if the ultrasonic measuring device is to be used for a new application. There is a particular preference for the acoustic window portion to have grip elements which are configured for the detachable fixing to the housing wall. The grip elements are lateral protrusions of the acoustic window portion which engage with suitable recesses in the housing wall. The grip elements advantageously facilitate a simple removal of the acoustic window portion from the housing, e.g. for replacement or cleaning purposes.

In accordance with a further embodiment of the invention, the acoustic window portion can advantageously be a disposable product. The acoustic window portion is configured for single use with a specific object, such as a specific test subject and/or a specific position on the surface of the object to be examined. Advantageously, troublesome cleaning or preparatory steps in the use of the ultrasonic measuring device for a new object and/or a new position on the object are avoided.

In accordance with a particularly preferred embodiment of the invention, it has proven to be sufficient, for example, for the acoustic window portion to be made of at least one plastic film. By special preference, the at least one plastic film is coated with a screening material. The plastic film can carry a layer made of a material which is suitable for electromagnetic screening. Furthermore, the at least one film can have a self-adhesive surface, i.e. at least one film is a self-adhesive foil. The acoustic window portion can, in particular, be composed of two or more films. For example, a first inner film can bear the screening material and a second outer film a self-adhesive film.

It has furthermore proved to be advantageous for the screening material to comprise, for example, an electrically conductive film or an electrically conductive mesh, conductive paints or glues or a metallic sputter layer, e.g. a zinc, aluminium, gold, copper or titanium sputter layer. The inventors have found that, for example, a sputter layer with a thickness of at least 10 nm and/or a maximum 1000 µm, is suitable to satisfy the screening function without impairing the transmission of ultrasonic signals.

In accordance with a variant of the invention, the ultrasonic array can be permanently connected with the housing. In this case, a particularly simple structure of the ultrasonic measuring device is advantageously provided. The direction of the sensitivity characteristic of the ultrasonic array can be set by the position and/or orientation of the ultrasonic measuring device during its positioning on the object and/or by a selective control of transducer elements of the ultrasonic array.

In accordance with a preferred embodiment of the invention, it is provided that the ultrasonic array can be moved with an actuator device relative to the housing, in particular relative to the acoustic window portion. The ultrasonic array can be moved in the housing, e.g. rotated or swivelled, whilst the housing wall and the acoustic window portion remain immobile. Contrary to the conventional ultrasonic measuring head in accordance with U.S. Pat. No. 5,598,845 A in which the ultrasonic array can be moved only together with the housing, this embodiment of the invention provides the possibility of reliably fixing the ultrasonic measuring device on the object to be examined. The fixing is not impaired by adjusting the ultrasonic array because the housing and, in particular, the acoustic window portion which contacts the object remain immobile if the ultrasonic array is moved.

In accordance with a particularly preferred embodiment of the invention, the ultrasonic measuring device is provided with the electrically, mechanically, hydraulically or pneumatically controlled actuator device which is configured to set and/or move the ultrasonic array relative to an object to be examined. The actuator device is configured to set and/or move the ultrasonic array relative to the object to be examined. The movement, position and/or orientation of the ultrasonic array relative to the object can be set using the actuator device.

Furthermore, it is provided in this embodiment of the invention for the actuator device to be arranged in the housing. The housing wall can be of one piece so that it encloses the entire inner space, or it can be of several pieces so that the actuator device is arranged in one part of the inner space and the ultrasonic array in another part of the inner space. The accommodation of the actuator device in the housing of the ultrasonic measuring device advantageously produces a compact structure of the ultrasonic measuring device. Unlike the ultrasonic measuring head in accordance with U.S. Pat. No. 5,598,845 A, in which the housing with the ultrasonic array must be adjusted manually or using a separate drive unit, the ultrasonic measuring device is a compact component, the functions of which (detection of ultrasonic signals, emission of ultrasonic waves where applicable, alignment of the ultrasonic array relative to the object to be examined) can be electrically controlled completely via a connection line, for example. During the use of the ultrasonic measuring device, particularly in fixed state to an object to be examined, the ultrasonic measuring device is not exposed to any mechanical forces when the ultrasonic array is moved which would impair the fixing on the object. The compact structure furthermore permits interference from the ultrasonic measuring device which could have an effect on a further device such as an MRI apparatus to be minimised or completely suppressed.

In accordance with a particularly preferred embodiment of the invention, the housing has a dual function. Firstly, it forms the above mentioned mechanical holder for the ultrasonic array and the actuator device. Secondly, it forms an encapsulation of the ultrasonic array and of the actuator device, in particular an electromagnetic screening (shielding). Preferably, the electromagnetic screening is a barrier for electromagnetic fields in the surrounding area of the ultrasonic measuring device. Furthermore, the screening provides a barrier for electromagnetic fields which are generated in the inner space of the housing and which could disturb the operation of a further device. The electromagnetic screening is configured in a particularly preferred embodiment such that it is effective against fields in a MRI apparatus, which for example has a static magnetic field of at least 1.5 T, for example 3 T, 7 T or 12 T.

The electromagnetic screening has proved to be particularly effective if at least one of the following measures is provided. In accordance with a first variant, a dual screening of the ultrasonic array and of the actuator device can be provided. The dual screening comprises a first shield on ground potential and a second shield to dampen electromagnetic fields from the environment of the ultrasonic measuring device. Secondly, a balun can be provided alternatively or additionally using which the electromagnetic waves on the connecting line are dampened such that electromagnetic fields are not emitted into the surrounding area. Advantageously, any antenna effect of the ultrasonic measuring device is suppressed. The dual screening has the special advantage that the outer screening independently of the inner screening of the ultrasonic array can have the potential in the field, e.g. of an MRI apparatus. An undesirable influencing of the field in the MR space can therefore be advantageously avoided.

The actuator of the inventive ultrasonic measuring device comprises generally an electrically operated drive with which the ultrasonic array is connected. For example, an electrically operated motor is provided with which the ultrasonic array can be rotated or pivoted via a drive shaft. In accordance with a specially preferred embodiment of the invention, the actuator comprises a piezoelectric ring motor with which the ultrasonic array can be moved relative to the acoustic window portion. The piezoelectric ring motor comprises at least two piezoelectric actuators and a rotor which is coupled with the ultrasonic array via the drive shaft. The piezoelectric ring motor offers advantages in terms of a particularly compact and light-weight structure of the ultrasonic measuring device as well as good suitability for use in an MRI apparatus.

Different possibilities advantageously exist to adjust the ultrasonic array in the housing. Firstly, the ultrasonic array can be rotatable around an axis parallel to a surface normal of the acoustic window portion, i.e. vertical to a plane acoustic window portion, or parallel to the surface normal in the centre of a curved acoustic window portion. In this case, the drive shaft of the electrical motor is aligned vertically to the acoustic window portion. Alternatively, in accordance with a second variant the ultrasonic array can be rotatable around an axis which is inclined relative to the surface normal of the acoustic window portion and runs in particular vertically relative to the surface normal of the acoustic window portion (i.e. parallel to a plane acoustic window portion or vertically to the surface normal in the centre of a curved acoustic window portion). In this case, the drive shaft of the electrical motor is inclined relative to the surface normal of the acoustic window portion. In accordance with further alternatives, the ultrasonic array with the actuator device can be shifted translationally. In particular, a shift along at least one of the specified axes can be provided.

Special advantages for the combination of the ultrasonic measuring device with an MRI apparatus result if the ultrasonic measuring device, in particular the ultrasonic array and the housing, are made of magnetic-resonance-compatible materials. If an actuator device is provided, this is also made of magnetic-resonance-compatible materials. A disturbance to the operation of the MRI scanner is advantageously minimised or excluded by a structure consisting of magnetic-resonance-compatible materials. Magnetic-resonance-compatible materials are materials which do not emit or emit only negligible magnetic-resonance signals in response to high-frequency fields occurring in the MRI apparatus. By way of special preference, the magnetic-resonance-compatible materials comprise piezoceramics, such as PZT (lead-zirconate-titanate ceramic), piezoelectrically active monocrystals or plastic films (PVDF, copolymers), a composite material (e.g. 3-1 PZT composites) made of plastic and metallic oxide and/or metallic powder, in particular aluminium oxide and/or tungsten powder, copper, zinc, conductive adhesive, in particular with silver particles, and/or plastic, such as POM (polyoxymethylene), PEEK (polyetheretherketone), PU (polyurethane), silicon, PET (polyethylene terephtalate), PC (polycarbonate) or epoxy resin.

Further advantageous modifications of the inventive ultrasonic measuring device result if this contains a sensor device using which geometric parameters of the ultrasonic measuring device can be recorded. In accordance with a first variant, the sensor device comprises a directional sensor with which the current alignment of the ultrasonic array in the housing, in particular relative to the acoustic window portion, can be detected. The directional sensor advantageously facilitates the detection of the sensitivity characteristic without an ultrasonic measurement needing to be made. Alternatively or additionally, the sensor device in accordance with a further variant comprises a position sensor with which the position of ultrasonic measuring device in the room, in particular relative to a further ultrasonic measuring device and/or to the object to be examined and/or relative to a further device such as an MRI apparatus, can be detected. The position sensor facilitates the use of the ultrasonic measuring device particularly in multimodal imaging or in the combination with radiotherapy methods.

In accordance with a further advantageous embodiment of the invention, the ultrasonic measuring device is provided with a shielded electrical line connection via which the ultrasonic array and the actuator device can be coupled with a control device. The line connection can comprise several or preferably one single cable, whereby the complete functions of the ultrasonic measuring device, particularly with respect to the generation and/or detection of ultrasonic signals and the setting of the ultrasonic array, can be controlled with the control device.

A main application of the ultrasonic measuring device is ultrasound-based imaging. Here, the ultrasonic array is used both as emitter of ultrasonic waves and as detector of ultrasonic waves in order to generate images of the area to be examined from the ultrasonic signals detected. However, it is not necessary for the ultrasonic signals to be generated by an emission of ultrasonic waves into the object. Alternatively, photoacoustic imaging is possible for example in which ultrasonic signals are detected which, as a reaction to irradiation of the area to be examined, are generated with pulsed light. In accordance with a further advantageous embodiment of the invention, it is intended for the coupling in of the pulsed light for the ultrasonic measuring device to be provided with an optic fibre device and/or at least one light source using which light can be directed in particular through the acoustic window portion and/or the housing wall onto the object to be examined.

In accordance with a second general aspect, the above described objective is solved by an examination apparatus which has at least one ultrasonic measuring device in accordance with the above specified first aspect. Preferably, the examination apparatus comprises several ultrasonic measuring devices. If, in accordance with a further preferred variant, the ultrasonic measuring devices are connected with a joint control device, advantages arise for the operation of the ultrasonic measuring devices and the analysis of the recorded ultrasonic signals. In accordance with a particularly preferred embodiment of the invention, the examination apparatus is arranged for operation in combination with an MRI tomography device or radiation therapy system.

In accordance with a third aspect of the invention, the above specified objective is solved by a method to detect ultrasonic signals, in particular for ultrasound-based imaging which comprises the following steps. Firstly, at least one ultrasonic measuring device in accordance with the above-stated first aspect of the invention is positioned on the surface of an object to be examined. A fixing of the at least one ultrasonic measuring device is preferred using the self-adhesive acoustic window portion. If an actuator device is provided, in a further step the ultrasonic array of the at least one ultrasonic measuring device is set. The ultrasonic array is aligned such that the sensitivity characteristic is directed at a desired area of the object to be examined. Furthermore, the at least one ultrasonic measuring device is actuated after adjustment or during the movement of the ultrasonic array, e.g. activated for an ultrasound-based imaging for an emission and receive operation or for a photoacoustic imaging for receive operation.

Figure 2:
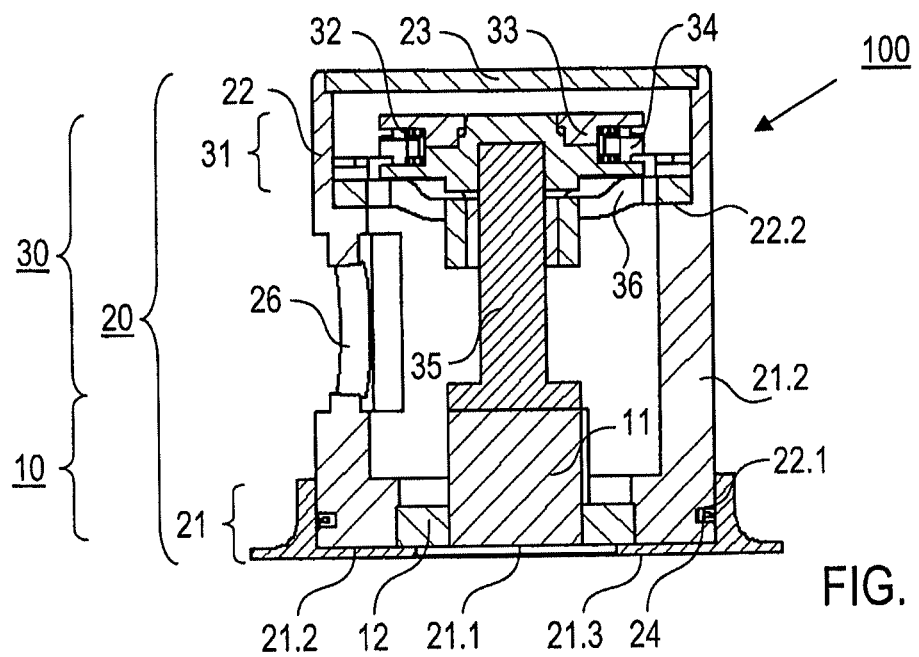
Figure 3:
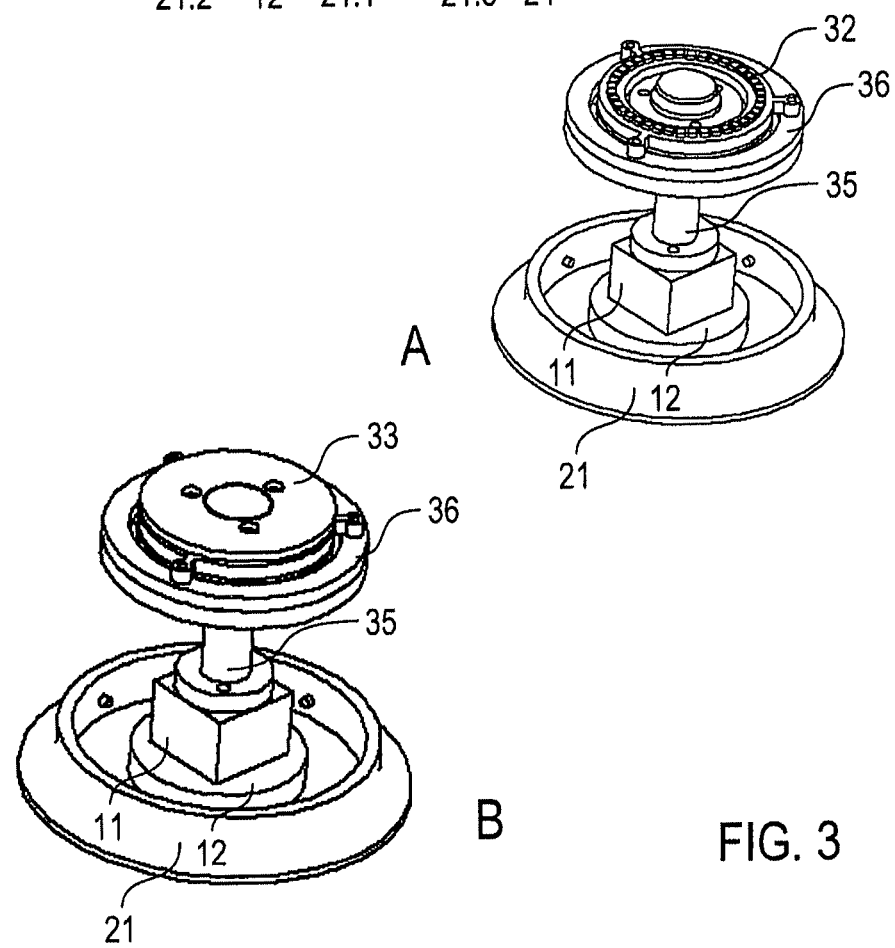
Figure 4:
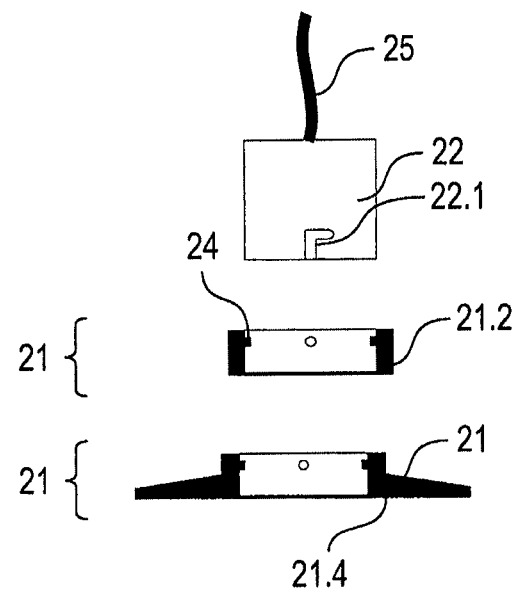
Figure 5:
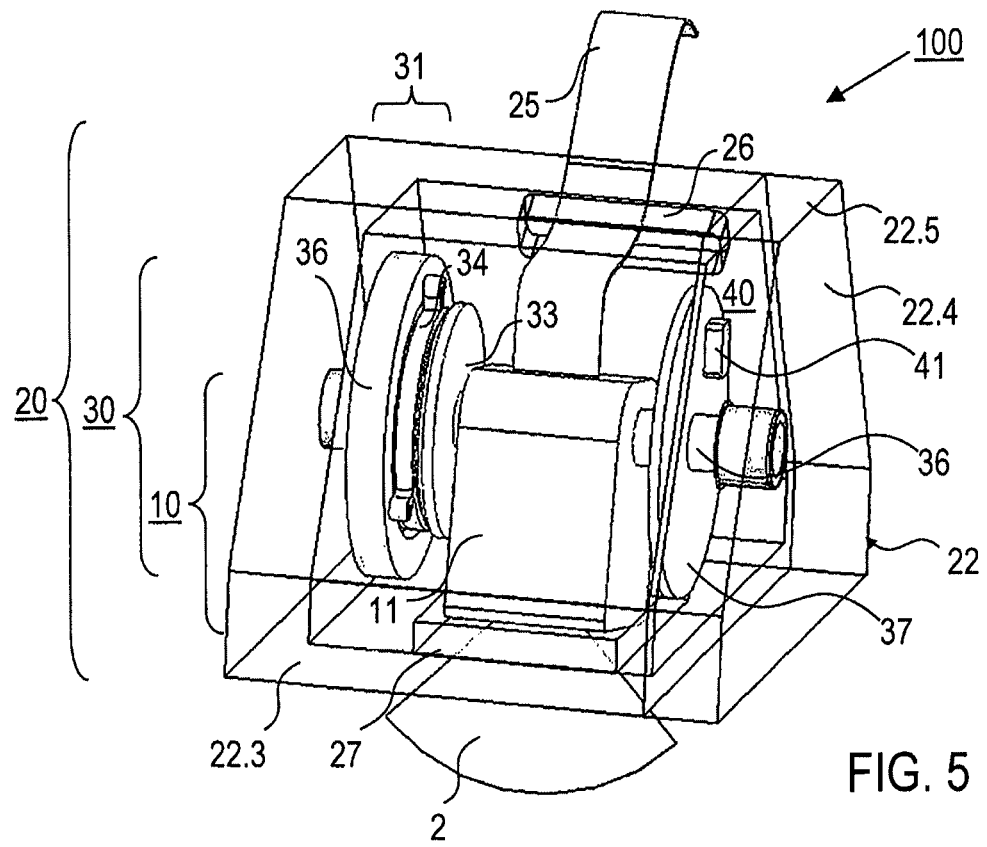
Figure 6:
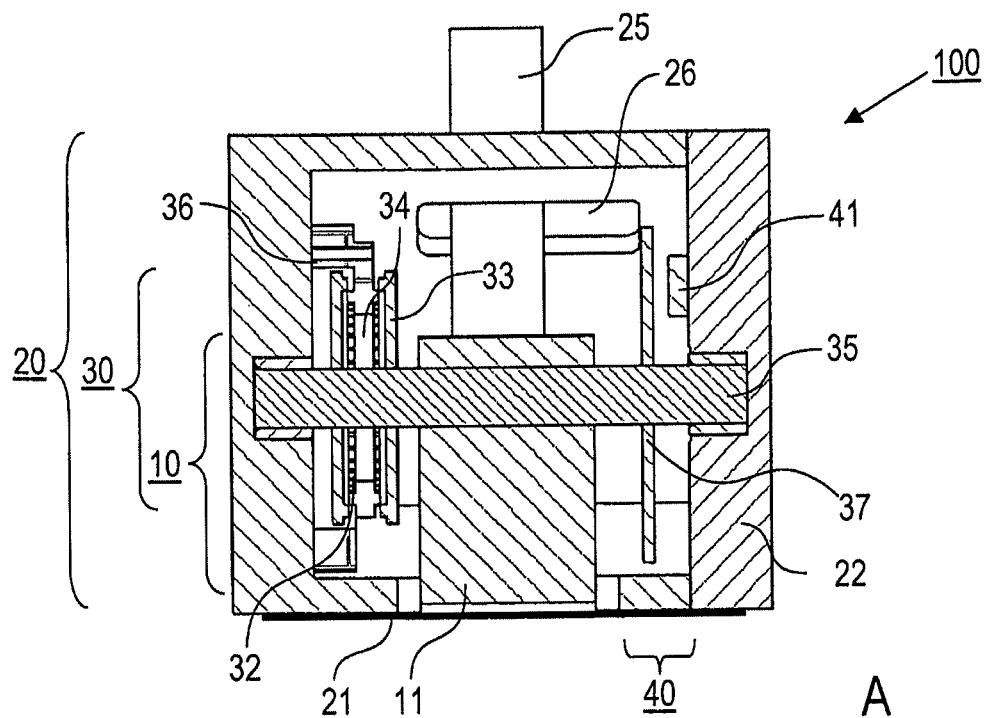
Figure 6:
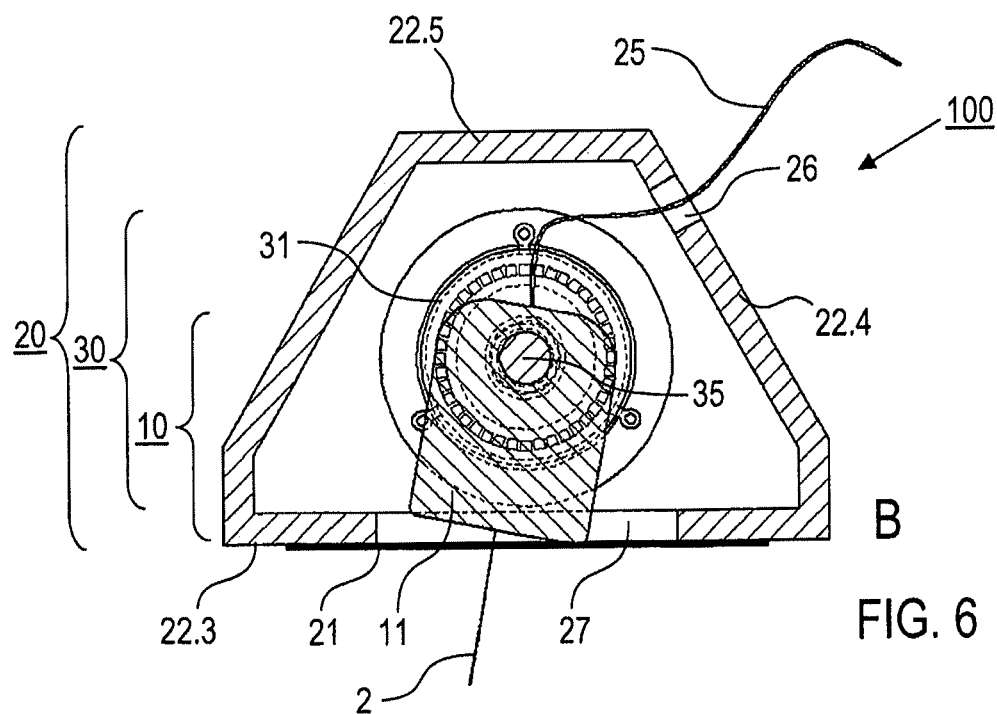
Figure 7:
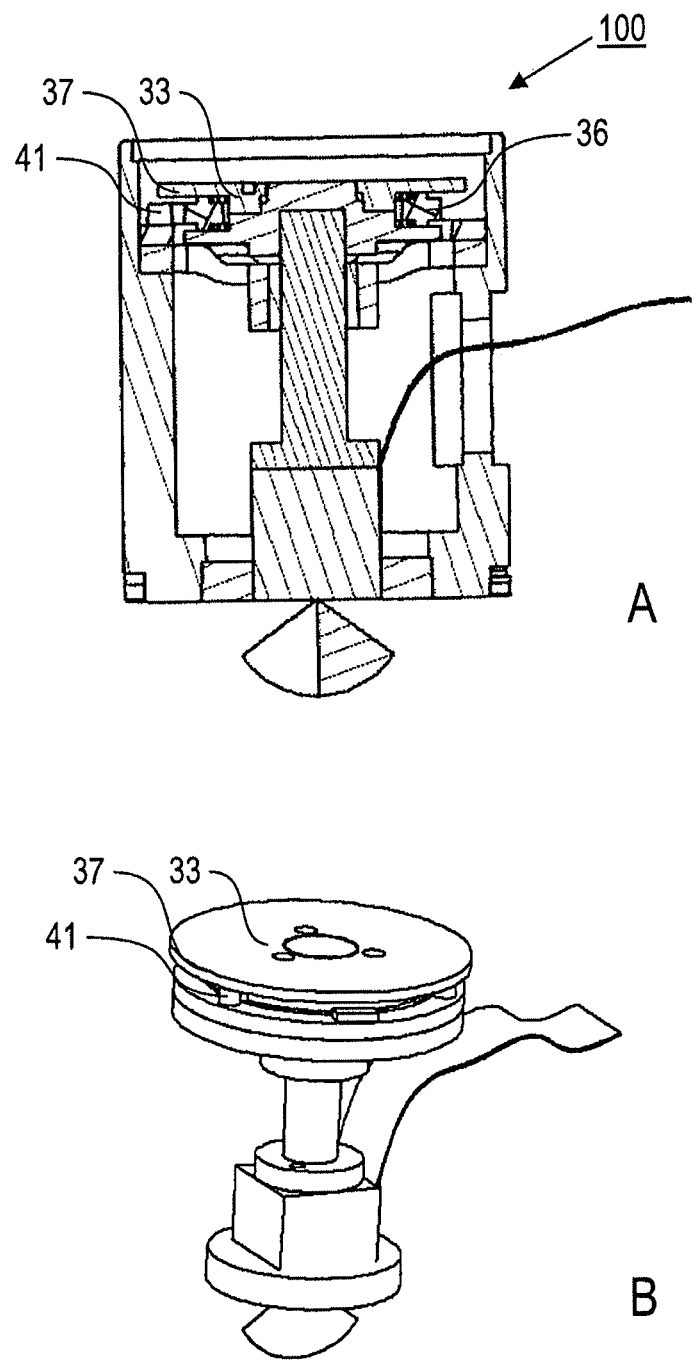
Figure 8:
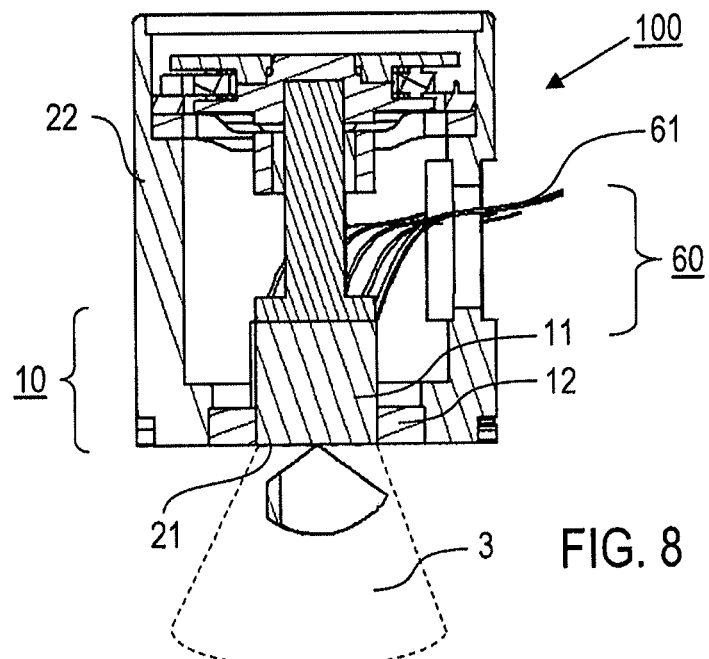
Figure 9:
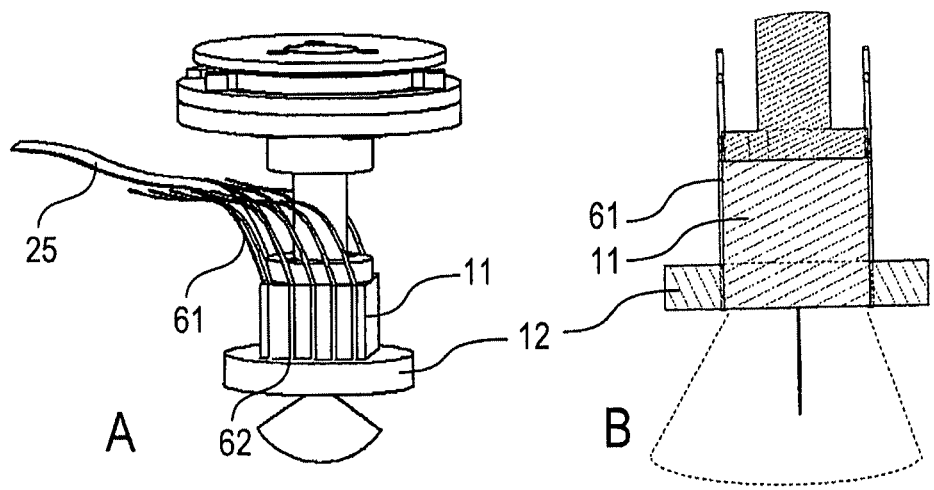
Figure 9:
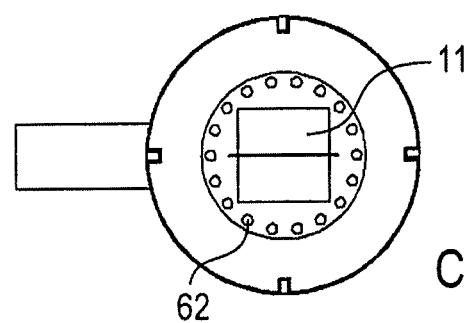
Figure 10:
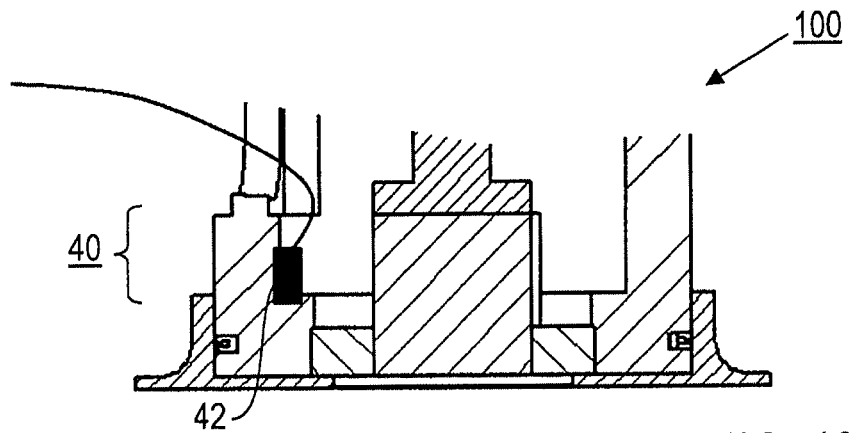
Figure 11:
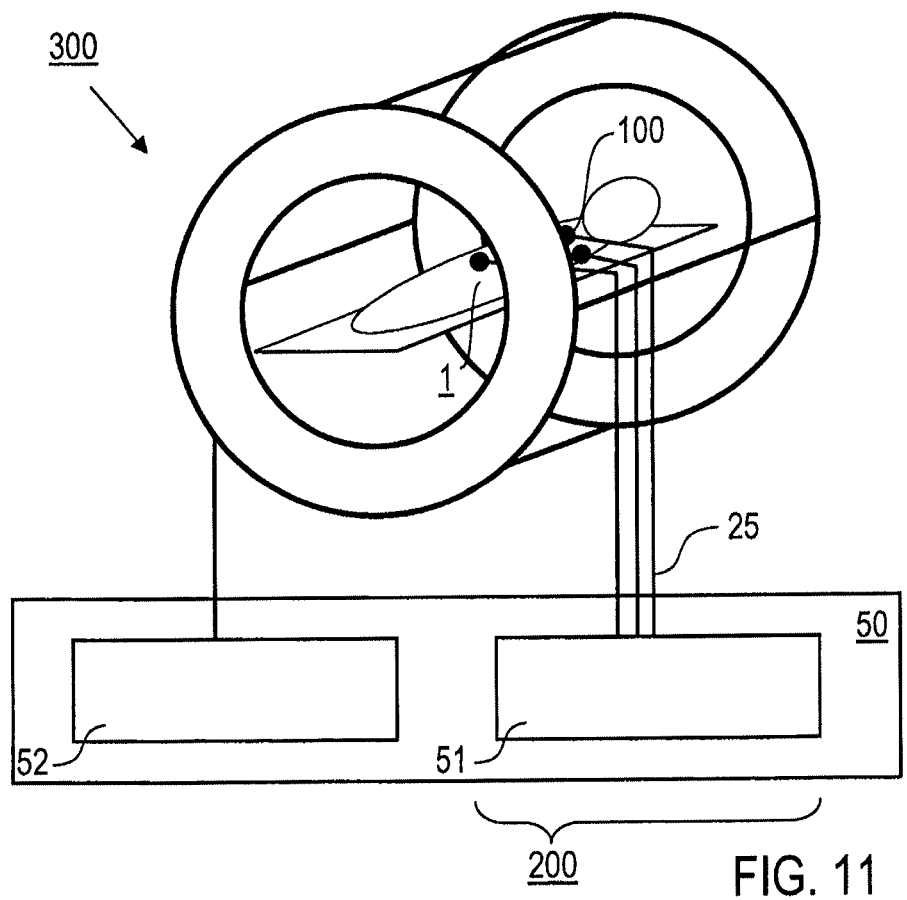

Further details and advantages of the invention are described in the following with reference to the attached drawings. The following are shown:

FIG. 1: a diagrammatic phantom presentation of a first embodiment of the inventive ultrasonic measuring device;

FIGS. 2 and 3: diagrammatic illustrations of a further embodiment of the inventive ultrasonic measuring device with vertical rotating axis of the ultrasonic array;

FIG. 4: diagrammatic illustration of variants of the acoustic window portion of an inventive ultrasonic measuring device with replacement functionalities;

FIGS. 5 and 6: diagrammatic illustrations of a further embodiment of the inventive ultrasonic measuring device with horizontal rotating axis of the ultrasonic array;

FIG. 7: diagrammatic illustrations of a further embodiment of the inventive ultrasonic measuring device which is provided with a directional sensor;

FIGS. 8 and 9: diagrammatic illustrations of a further embodiment of the inventive ultrasonic measuring device which is provided with an optic fibre device;

FIG. 10: an illustration of the provision of a position sensor in an inventive ultrasonic measuring device; and FIG. 11: a diagrammatic illustration of the combination of an inventive examination apparatus with an MRI apparatus.

Embodiments of the invention are described in the following with reference by way of example to an ultrasonic measuring device which is configured as an ultrasonic measuring head for ultrasonic imaging or photoacoustic imaging, particularly in combination with an MRI apparatus. It is emphasised that the application of the invention is not restricted to the examples given but is possible in accordance with other forms of multimodal imaging or other applications of ultrasound, particularly in combination with (radio) therapy methods. Depending on the specific application of the invention, the ultrasonic measuring device can be provided if required with an electromagnetic screening. The majority of the embodiments of the invention show the ultrasonic measuring device with an ultrasonic array which can be moved in the housing and an actuator device. However, the implementation of the invention is not restricted to these embodiments but is also possible with a rigidly arranged ultrasonic array in the housing. Details of the structure and operation of an ultrasonic array, particularly for imaging purposes, and of an MRI apparatus are not described here because these are known from the state of the art.

FIG. 1 diagrammatically illustrates a first embodiment of the ultrasonic measuring device 100 in a perspective view. The ultrasonic measuring device 100 comprises an ultrasonic array 10 which together with an actuator device 30 is arranged in a housing 20. The ultrasonic array 10 and the actuator device 30 in the inner space of the housing 20 are shown diagrammatically in broken lines for the purposes of illustration. Further details of these components are described further below with respect to the other figures.

The housing 20 comprises an acoustic window portion 21 and a housing wall 22, 23 with which a connecting line 25 for the electrical connection of the ultrasonic array 10 and of the actuator device 30 is coupled with a control device (not shown, see FIG. 11). The housing 20 has a conical shape, the diameter of which reduces from the acoustic window portion 21 towards a cover part 23. The cover part 23 is a part of the housing wall 22 which can be opened for maintenance or control purposes as required. The side of the ultrasonic measuring device 100 facing the object 1 to be examined, in particular the side of the housing 20 with the acoustic window portion 21, is described as lower side here without restricted effect whilst the other side is described as the upper side. However, when the ultrasonic measuring device 100 is used it is not necessary for the lower side to point in gravitational direction. The housing wall 22 is not shown in some of the figures described below.

The ultrasonic measuring device 100 has the following dimensions, for example: diameter of the acoustic window portion 21: 4 cm, diameter of the cover part 23: 2 cm, height of the housing 20: 2 cm, weight of the housing 20 with ultrasonic array 10 and the actuator device 30: 30 g. The housing wall 22 and the cover part 23 are made, for example, from copper or a plastic coated with copper.

The acoustic window portion 21 has a plane film 21.1, for example made of PEEK, with a thickness of 100 μm. The film 21.1 is fixed in a holding frame 21.2 made, for example, of copper or a plastic coated with copper, with a circumferential edge, the inner diameter of which is matched to the outer diameter of the housing wall 22. The edge carries the grip elements 24 which are shown in FIGS. 2 and 4. The acoustic window portion 21 forms a cap which can be set onto the housing wall 22 and which can be replaced as required. The film 21.1 is, for example, a self-adhesive film made by 3M, USA.

If an electromagnetic screening of the inner space of the housing is required, the film 21.1 is provided on one side, for example with an electrically conductive layer (e.g. sputter layer made of aluminium, copper, gold, titanium, zinc, etc.) which is electrically connected via the holding frame 21.2 with the screening of the housing wall 22. The electrically conductive layer is preferably provided on the inner side of the film 21.1.

The screening preferably comprises a dual screening of the ultrasonic array 10 and of the actuator device 30. The first shield on ground potential is, for example, formed by the housing wall of copper and the electrically conductive layer. The second shield to dampen electromagnetic fields from the environment of the ultrasonic measuring device is formed, for example, by a sheath made of aluminium and/or copper which extends from the connection line 25 to the ultrasonic array 10. A sheath current filter is provided alternatively or additionally between the housing 20 and the connection line 25.

An adhesive layer is provided on the outer side of the acoustic window portion 21 on film 21.1 and/or the holding frame 21.2 using which the ultrasonic measuring device 100 can be fixed to a body section of the object 1 to be examined. The object 1 (shown partially in FIG. 1) is, for example, the body of test subject in medical imaging or a material to be examined using ultrasound.

For the use of the ultrasonic measuring device 100 it is adhered with the acoustic window portion 21 to the surface of the object 1 to be examined. The alignment of the ultrasonic array 10 is set using the actuator device 30. The ultrasonic array 10 is turned in the inner space of the housing 20 and/or shifted in a translatory manner, for example, such that the sound field 2 has a predefined alignment in a region to be examined in the object 1. Finally, the ultrasonic array 10 is operated, i.e. the emission of a sound field 2 of ultrasonic waves into the area to be examined and the detection of back-reflected ultrasonic waves, the transmission of the detected ultrasonic signals to the control device and signal processing to generate ultrasonic images.

Alternatively, the ultrasonic measuring device 100 facilitates data recording during the motion of the ultrasonic array 10, e.g. for a volume detection of 3D imaging. For example, it can be provided that the ultrasonic array 10 permanently rotates during operation of the ultrasonic array 10 for data recording.

In an embodiment with a rigidly arranged ultrasonic array 10 in the housing 20, the ultrasonic measuring device 100 is structured as described above whereby, however, the actuator device 30 is replaced by a fixed holder of the ultrasonic array 10 in the housing 20.

Further details of an embodiment of the ultrasonic measuring device 100 with vertical axis of rotation of the ultrasonic array 10 are shown in FIGS. 2 and 3A, 3B. FIGS. 3A, 3B illustrate the connection of actuator device 30 and ultrasonic array 10 without the housing wall 22. In accordance with the diagrammatic cross-sectional view in FIG. 2, the housing 20 comprises the acoustic window portion 21 and the housing wall 22 with the cover part 23. The housing wall 22 has a cylindrical shape with a lateral opening 26 for the attachment of the connection line (not shown in FIG. 2). The housing wall 22 has recesses 22.1 in the edge facing the acoustic window portion 21 to accommodate the grip elements 24 of the acoustic window portion 21 (see also FIG. 4). A peripheral edge 22.2 is provided in the inner side of the housing wall 22 in an upper inner space facing the cover part 23, which forms a holder for the actuator device 30.

The acoustic window portion 21 is connected with the housing wall via the holding frame 21.2 and the grip elements 24. The holding frame 21.2 has an adhesive layer 21.3 on its free surface which is provided to fix the ultrasonic measuring device 100 on the object to be examined.

The ultrasonic array 10 comprises a group of ultrasonic transducer elements 11 and a mounting 12. The ultrasonic transducer elements 11 each comprise a defined number of individual elements and arrangements with a defined geometric size and operational frequency depending on case of application. The mounting 12 has, for example, the shape of a cylindrical disc (see FIG. 3A, 3B) into which the ultrasonic transducer elements 11 are recessed. The mounting 12 has a dual function. Firstly, a surface of the mounting 12 forms a support area together with the radiation side of the ultrasonic transducer elements 11. In the assembled state, the inner side of the acoustic window portion 21 touches the support area of the ultrasonic array 10. For the improved transmission of ultrasonic waves, a transmission medium such as a gel, oil or fat can be provided between the ultrasonic array 10 and the acoustic window portion 21. Where required, the transmission medium can be replaced or renewed when replacing the acoustic window portion 21, for example. Secondly, the mounting 12 forms a fixing point for further components such as the fibre optic of a fibre optic device (see FIG. 7).

The actuator device 30 is held in the housing 20 on the edge 22.2. The actuator device 30 comprises a piezoelectric ring motor with piezo actuators 32, a rotor 33, a stator 34, a drive shaft 35 and a bearing 36. The first end of the drive shaft 35 is connected with the rotor 33 and the second end with the ultrasonic array 10, in particular the ultrasonic transducer elements 11. The ultrasonic transducer elements 11 are stuck or screwed to the drive shaft 35.

The piezo actuators 32 are arranged in a ring shape. When an excitation voltage is applied to the piezo actuators 32, the rotor 33 can be caused to turn with the drive shaft 35 and the ultrasonic array 10 around the vertical axis (z-axis). As shown in FIG. 3, the piezo actuators 32 form two groups which on the one hand are arranged in the shape of a ring on the stator 34 (FIG. 3A) and on the other hand in the shape of a ring on the rotor 33 (FIG. 2, FIG. 3B). It is not absolutely necessary for the piezo actuators 32 to be arranged evenly along the entire circumference of the rotor 33 and of the stator 34. Depending on the use of the invention, it may be sufficient to provide individual piezo actuators for gradual adjustments of the ultrasonic array 10.

Contrary to the illustration, the actuator device 30 may be designed for a translatory movement and have a piezoelectric linear drive (not shown).

FIG. 4 diagrammatically illustrates different variants of the acoustic window portion 21. For example, the holding frame 21.2 can be restricted to a circumferential edge on the inner side of which the grip elements 24 are provided. Alternatively, the holding frame 21.2 may extend in a radial direction in order to form a circular adhesive area 21.4.

The recesses 21.2 on the outer side of the housing wall 22 comprise an angled groove to accommodate the grip elements 24. The holding frame 21.2 is pushed onto the housing wall 22 to fix the acoustic window portion 21 to the housing wall 22 such that the grip elements 24 engage in the recesses 22.1. By turning the acoustic window portion 21 and the housing wall 22 relative to each other, the acoustic window portion 21 is anchored in the housing wall 22.

FIGS. 5 and 6 illustrate a modified embodiment of the inventive ultrasonic measuring device 100 with a horizontally aligned rotating axis of the ultrasonic array 10. FIG. 5 shows a perspective phantom view whilst FIGS. 6A and 6B show cross-sections parallel and vertical to the rotating axis. In this embodiment of the invention, the housing wall 22 of the housing 20 comprises a plane basic area 22.3, plane and angled side areas 22.4 and a cover area 22.5. The acoustic window portion 21 is connected with the basic area 22.3, e.g. recessed into it or set on top of it (see FIG. 6B). In one of the side areas 22.4, there is an opening 26 to lead through or couple a connection line 25. A recess is formed with the opening 27 in the basic area 22.3 to the acoustic window portion 21 into which the parts of the ultrasonic array 10 protrude when swivelled. To improve the ultrasonic coupling, the recess in the opening 27 can be filled with a transfer medium such as a gel, fat or oil.

As described above with respect to the FIGS. 2 and 3, the actuator device 30 comprises a piezoelectric ring motor 31 with piezo actuator devices 32, a rotor 33, a stator 34, a drive shaft 35 and a bearing 36. The piezoelectric ring motor 31 is arranged such that the rotating axis of the drive shaft 35 runs parallel to the basic area 22.3. The drive shaft 35 rotates on the facing inner sides of the side areas 22.4. The ultrasonic array 10 is attached to the drive shaft 35 and can be swivelled around the rotating axis on actuation of the piezoelectric ring motor 31 (FIG. 6B) so that the sound field 2 points in different directions in the object to be examined.

FIGS. 5 and 6A show a sensor device 40 at the end of the drive shaft 35 to detect geometrical parameters of the ultrasonic measuring device 100, in particular of the ultrasonic array 10. In the embodiment shown, the sensor device 40 comprises an optical directional sensor 41 which is arranged on the inner side of the side area 22.4. A clock disc 37 with a pattern is positioned on the drive shaft 35, whereby the position of the clock disc is detected using the directional sensor 41.

In this embodiment of the ultrasonic measuring device 100 too, the directional sensor 41 can have a vertical rotating axis as shown diagrammatically in FIGS. 7A and 7B. In this case, the clock disc 37 is connected with the rotor 33 whilst the directional sensor 41 is positioned on the stator 34, for example.

FIGS. 8 and 9 illustrate an embodiment of the inventive ultrasonic measuring device 100 which is configured for photoacoustic imaging. In this case a fibre optic device 60, comprising a plurality of optical fibres 61, is provided which, for example, is led to the ultrasonic array 10 as part of the connecting line 25 or additionally to it. The end sections of the optical fibres 61 are fixed to the ultrasonic transducer elements 11 and/or in the mounting 12 such that the outgoing ends 62 of the optical fibres 61 face the acoustic window portion 21. Typically, a plurality of optical fibres 61 is provided which form a pattern with several straight rows of point wise excitation light sources (diagrammatic perspective view in FIG. 9A, cross-sectional view in FIG. 9B), a rectangular pattern or a circular pattern (top view in FIG. 9C) of pointwise excitation light sources. The optical fibres can be provided with optical elements, e.g. optical lenses, e.g. to focus excitation light. Alternatively, the optical fibres can be fixed to the housing wall 22. The optical fibres 61 can also be arranged such that the outgoing ends 62 are exposed towards the outer side of the housing 20. A pulsed excitation light 3 is coupled in to the object to be examined via the optical fibres 61. The mechanical oscillations generated in response to the excitation in the object to be examined are detected as ultrasonic oscillations by the ultrasonic array 10.

Deviating from the illustration, light sources such as LEDs can be arranged in and/or outside the housing 20 in order to generate the excitation light to be coupled in to the object to be examined (not shown).

The sensor device 40 in accordance with a further variant of the invention can comprise a position sensor 42 which is shown diagrammatically in FIG. 10. Using the position sensor 42 which is integrated in the inside or, deviating from the illustration in FIG. 10, can be attached to the outer side, the spatial position of the ultrasonic measuring device 100 can be detected, for example relative to an adjacent MRI apparatus or to a holding platform for the object to be examined. The position sensor 42 is, for example, set up to detect pulsed high frequency signals from a group of antennas in the surrounding area of the ultrasonic measuring device 100. Following calibration, all positions of ultrasonic measuring devices can be detected in a global reference system and coordinated with the geometrical parameters of other devices.

FIG. 11 provides a diagrammatic illustration of an embodiment of an inventive examination apparatus 200 with a plurality of ultrasonic measuring devices 100 which are arranged on a test subject 1 for simultaneous or sequential ultrasonic imaging. The test subject 1 is in an MRI tomography device 300. The ultrasonic measuring devices 100 are connected with a control device 50 via connection lines 25. The control device 50 contains a first operating circuit 51 for the operation of the ultrasonic measuring devices 100 and a second operating circuit 52 to operate the MRI tomography device 300. The images obtained using the examination apparatus 200 and the MRI tomography device 300 can be registered with each other and subjected to a further analysis, image processing and/or display. It is not absolutely necessary for the first and second operating circuits 51, 52 to be connected in a common control device 50. The examination apparatus 200 and the MRI tomography device 300 may be connected using separate operating circuits.

The features of the invention disclosed in the description, the drawings and the claims may be of importance both individually and also in combination for the realisation of the invention in their different embodiments.

The invention claimed is:

1. An ultrasonic measuring device, comprising:
   an ultrasonic array configured to detect ultrasonic signals, wherein the ultrasonic array is arranged both as an emitter of ultrasonic waves and as a detector of ultrasonic waves in order to generate images of an area to be examined from the ultrasonic signals detected,
   a housing comprising an acoustic window portion and a housing wall, the ultrasonic array being arranged in the housing in acoustic contact with the acoustic window portion,
   an electrically actuated actuator device which comprises a piezoelectric ring motor being enclosed by the housing and which is configured for an adjustment and movement of the ultrasonic array relative to the acoustic window portion and the area to be examined, wherein the piezoelectric ring motor comprises at least two piezoelectric actuators and a rotor which is coupled with the ultrasonic array via a drive shaft, and
   a position sensor using which a spatial position of the ultrasonic measuring device can be detected, and
   a directional sensor using which the alignment of the ultrasonic array in the housing can be detected, wherein the acoustic window portion is a plastic film which allows a transmission of ultrasonic waves, and comprises an external surface provided with an adhesive material such that the acoustic window portion is configured for an adherence to a surface of the object to be examined, the housing forms an electromagnetic shielding comprising a screening of the ultrasonic array and the piezoelectric ring motor and a balun at a line connection coupled with the housing, wherein the electromagnetic shielding is effective against fields in an MRI tomography device, and the ultrasonic array, the piezoelectric ring motor and the housing are made of magnetic-resonance-compatible materials that do not emit or emit negligible magnetic-resonance signals in reaction to high-frequency fields occurring in an MRI scanner.

2. The ultrasonic measuring device in accordance with claim 1, in which the acoustic window portion has at least one of the following features:
the acoustic window portion being arranged detachably from the remaining housing,
the acoustic window portion being a disposable product,
the plastic film of the acoustic window portion has a screening material, and
the acoustic window portion having a self-adhesive film.

3. The ultrasonic measuring device in accordance with claim 2, in which
the plastic film has the screening material, and
the screening material comprises an electrically conductive sputter layer or is made of conductive material.

4. The ultrasonic measuring device in accordance with the claim 2, in which the acoustic window portion is detachably attached via grip elements to the housing wall.

5. The ultrasonic measuring device in accordance with claim 1, including at least one of the following features:
the ultrasonic array can be rotated around an axis parallel to a surface normal of the acoustic window portion,
the ultrasonic array can be rotated around an axis which is inclined relative to a surface normal of the acoustic window portion, and
the ultrasonic array is movable in a translatory manner.

6. The ultrasonic measuring device in accordance with claim 1, in which the magnetic-resonance-compatible materials comprise at least one of:
piezoceramics,
piezoelectrically active monocrystals,
piezoelectrically active polymers,
composite materials made of piezoelectrically active monocrystals and polymers,
composite material made of plastic and metallic oxide or metallic powder,
metal,
conductive adhesive, and
plastic.

7. The ultrasonic measuring device in accordance with claim 1, wherein the directional sensor is located within the housing, and the directional sensor is configured to detect the alignment of the ultrasonic array in the housing without an ultrasonic measurement.

8. The ultrasonic measuring device in accordance claim 1, further comprising at least one of a fibre optic device and at least one light source using which light can be directed through at least one of the acoustic window portion and the housing wall onto the object to be examined.

9. An examination apparatus comprising at least one ultrasonic measuring device in accordance with claim 1, and a control device arranged to operate the at least one ultrasonic measuring device and to analyze recorded ultrasonic signals.

10. The examination apparatus in accordance with claim 9, which is arranged in connection with an MRI tomography device.

11. The ultrasonic measuring device in accordance with claim 1, in which the magnetic-resonance-compatible materials comprise at least one of:
piezoceramics,
piezoelectrically active monocrystals,
piezoelectrically active polymers,
composite materials made of piezoelectrically active monocrystals and polymers,
composite material made of plastic and metallic oxide or metallic powder,
metal,
conductive adhesive, and
plastic.

12. The ultrasonic measuring device in accordance with claim 1, further comprising a connection line coupled to the ultrasonic array and to a control device arranged to operate the ultrasonic measuring device.

13. A method for ultrasonic signal detection, comprising:
arranging the external surface of the acoustic window portion of the ultrasonic measuring device in accordance with claim 1 on the surface of an object to be examined; and
actuating the at least one ultrasonic measuring device to transmit ultrasonic waves through the acoustic window portion to the surface of the object to be examined.

14. The method in accordance with claim 13, in which the at least one ultrasonic measuring device is actuated for ultrasound-based imaging.

15. The method in accordance with claim 13, in which the at least one of the positioning and continuously moving is conducted for scanning the at least one ultrasonic measuring device for a 3D data detection.

16. The method in accordance with claim 13, further comprising:
arranging the object to be examined in an MRI tomography device, and
conducting the ultrasound-based imaging during the operation of the MRI tomography device.

* * * * *